United States Patent [19]

Gilbert

[11] Patent Number: 4,867,150
[45] Date of Patent: Sep. 19, 1989

[54] PERFORATED ELASTOMERIC SOFT FILM AND WOUND DRESSING MADE THEREWITH

[75] Inventor: Eugene C. Gilbert, Brecksville, Ohio

[73] Assignee: The B. F. Goodrich Company, Akron, Ohio

[21] Appl. No.: 5,006

[22] Filed: Jan. 20, 1987

[51] Int. Cl.[4] .................. A61F 13/00; A61F 15/00
[52] U.S. Cl. .................. 128/155; 128/156; 428/286; 428/425.1; 523/111
[58] Field of Search .............. 128/155, 156; 604/304, 604/307, 358, 370, 896, 897; 428/286, 425.1, 138; 523/111

[56] References Cited

U.S. PATENT DOCUMENTS

| | | | |
|---|---|---|---|
| 3,307,545 | 3/1967 | Surowitz | 128/156 |
| 3,927,669 | 12/1975 | Glatt | 128/156 |
| 4,051,848 | 10/1977 | Levine | 128/156 |
| 4,081,580 | 3/1978 | Kato | 428/138 |
| 4,541,426 | 9/1985 | Webster | 128/156 |
| 4,554,317 | 11/1985 | Behar et al. | 128/156 |
| 4,657,006 | 4/1987 | Rawlings et al. | 128/156 |
| 4,664,662 | 5/1987 | Webster | 128/156 |
| 4,686,137 | 8/1987 | Ward, Jr. et al. | 428/423.1 |

Primary Examiner—Richard J. Apley
Assistant Examiner—Paul Prebilic
Attorney, Agent, or Firm—Nestor W. Shust; Alfred D. Lobo; James R. Lindsay

[57] ABSTRACT

The perforations in a film-faced wound dressing have been discovered to have edges which, though clearly defined, lack the ability to cut the neoepithelium of a healing wound, with the result that the film affords an unexpectedly high degree of comfort during movement of the patient- and most particularly, when the dressing is changed. This occurs in a thin, soft, self-supporting elastomeric film, such as a polyether polyurethane (PPU) film, having less than 10% crystallinity. The film provides a degree of conformability not attained heretofore; has a softness and elastomeric quality which results in reduced shear associated with the edges of its perforations as compared with the sharp cutting edges of perforations in plastic film; has excellent releaase characteristics enhanced by less than 25% open area (due to perforations) which minimizes the open area into which the neoepithelium may grow.

14 Claims, 2 Drawing Sheets

PERFORATED ELASTOMERIC SOFT FILM AND WOUND DRESSING MADE THEREWITH

BACKGROUND OF THE INVENTION

This invention relates to a wound dressing made with a self-supporting elastomeric thin film of perforated polymer to be placed in contact with a wound. The film not only has excellent "release" properties, but also is so soft and "giving" as to permit being removed from the wound with a minimum of pain or trauma. The wound-contact properties of the film are such that it may be left in contact with the wound longer than would ordinarily be practical with minimal maceration of the neoendotheliazing wound bed and surrounding wound area. The wounds may be burns, lacerations, or post surgical wounds, which accounts for the dressing being referred to as a surgical dressing.

The function of such a dressing is to protect the wound and absorb exudate while maintaining permeability to oxygen to facilitate healing and avoid maceration of the skin. Such protection is effected, in part, with an absorbent pad, permeable to air, secured to the perforated thin film which is placed with its lower surface in direct contact with the wound to minimize the growth of neoepithelium (sometimes less correctly referred to as eschar) into the absorbent pad to which the neoepithelium would adhere. Such a dressing is referred to as a "pad only dressing", and is generally held in place with a cotton gauze bandage which is a separate article in relation to the dressing.

As used herein, the term "dressing" always refers to an absorbent pad of material in combination with the thin polymeric film bonded to at least one surface of the absorbent pad, and preferably both the upper and lower surfaces of the pad. It will be understood that as used herein, the term "lower surface" refers to the surface to be placed in contact with the wound, and the upper surface is spaced apart from the lower surface by the thickness of the absorbent pad. Since typically, both the upper and lower surfaces are faced with the film, the wound dressing is referred to in the art as a "film-faced wound dressing", though only the surface to be placed in contact with the wound may be faced with the film.

In some instances, to expedite bandaging the dressing to the wound, a modified form of the dressing is used in which the upper surface of the wound dressing is secured to an adhesive surface of a backing sheet. Typically, this is a skin-conformable thin laminar web of woven or nonwoven fabric made from a normally liquid-impervious, resilient synthetic resinous material. This backing sheet, referred to as 'backing', is preferably perforated (to breathe) adhesive tape or sheet, to hold the dressing on that part of the body which is wounded. The lower surface of the absorbent pad is faced with a perforated thin film placed in contact with the wound. Relatively narrow strips of backed dressings, from about 2 cm to about 4 cm wide, with releasable protective strips are used as finger bandages, of the type illustrated in U.S. Pat. No. 3,043,301 to Plantinga et al; wider ones about 6 cm×6 cm are used on larger areas of the body. Because the backing serves as a bandage which is united with and not separate from the dressing, this combination, in such a modified form, is referred to as a "backed dressing".

'Pad only', and 'backed' dressings of this general type in the prior art, each of which dressings utilizes a thin film in direct contact with the wound, are highly desirable. The pain of having such a dressing removed while the wound is healing is relatively remarkably less than with dressings which do not rely on a film (in contact with the wound) with specific "easy-off" properties for 'release' from the wound's surface. The term "film" is used herein to refer to the thin self-supporting elastomeric film which, in my invention, is to be placed in direct contact with the wound.

The film is typically adhesively secured to an absorbent pad, made from conventionally used non-toxic woven or non-woven fabric, optionally coated with a coating, or containing a layer, of a flexible hydrophilic material adapted to absorb exudate. The pad is, of course, the main component of such a wound-dressing. The more desirable dressings not only absorb exudate effectively, but breathe well to accelerate healing of the wound, and are easily removed without inflicting pain. As will readily be appreciated, the adhesive layer bonding the pad to the film must meet numerous requirements relating to toxicity, disintegration when wetted with exudate, and of which requirements contribute to the cost of adhesive, which cost, coupled with the cost of applying the adhesive, add up to a substantial portion of the cost of manufacturing a wound dressing of this type. It is desirable to minimize this cost.

Smooth perforated film is used in the art to provide good release from the healing wound, thus result in minimal tearing of the eschar or scab. This in turn causes less pain than that caused by removal of a dressing which does not have excellent release characteristics. But a film, such as Mylar polyester film with excellent release characteristics may have a highly undesirable cutting action during removal of the dressing.

However, even among films with acceptable release characteristics one cannot predict at which end of the scale of acceptability its release might be; nor can one predict if the film has other characteristics which mitigate against its use, for example degradation due to contact with exudate, or due to exposure to heat and light, and most of all whether the perforated film will be soft enough not to have a cutting action on a healing wound. Moreover, an imperforate soft film, whether plastic or elastomeric, may provide good release, but its good release is masked though not negated, When the !film is foraminous, that is, multiply perforated (referred to herein as "perforated" for brevity) and the multiplicity of perforations have jagged edges. In the prior art, the goal was to maximize the open area to minimize adhesion of the film to the neoepithelium, while ignoring the adverse effect of the number of perforations on the cutting action of the film. The patient simply suffered the trauma of removal of the wound dressing, and tried not to move until the dressing had to be changed.

We have now realized that, even with a film having excellent release, the goal must be to minimize the open area (due to perforations) to minimize the growth of neoepithelium into the perforations, yet not adversely affecting the required "breathability", and water or moisture vapor transmission rate (MVTR) of the film.

Recently there has become available a perforate, thin, soft elastomeric polyurethane film, which provides more than about 5% of open area relative to the overall area of film, without tearing or unacceptably distorting the peripheral edges of the perforations. If the open area is more than about 5%, but is limited to 25%, I have found that a soft elastomeric film from a variety of polymeric materials exhibit a comparable combination of desirable strength, good release characteristics, lack of cutting action, and breathability. This has made it possible to experiment with a wide variety of perforated soft elastomeric self-supporting polymeric films to find those with properties best suited for a film-facing on a wound dressing.

Known perforated thin films currently in use in such film-faced dressings are flexible and thermoplastic, but they are not elastomeric, and are therefore referred to as being "plastic" as opposed to "elastomeric". Typical synthetic resinous materials suggested in the prior art for such films have been polyethylene terephthalate, sold under the Mylar brand, polyethylene, poly(vinyl chloride) ("PVC"), cellulose acetate, poly(vinylidene chloride) and nylon. Their choice in wound dressings was dictated less by their release properties than their susceptibility to being easily perforated, referred to as "punchability" because the convenient and conventional method of perforating a thin plastic film is to punch through, or die-cut it with a mechanical punching means. As will be apparent, their punchability is attributable in large part to the crystallinity of the resin, and even PVC which is regarded as being amorphous, or having low crystallinity relative to the other resins, when punched, results in a film having holes with peripheries which can cut, whether the peripheries are well defined or not.

Most of all, it was never suggested that the cost of securing the film to the absorbent pad may be minimized by eliminating the adhesive, and that this could be accomplished by selecting a film of a polymer which is thermally bondable to the pad without being degraded. But before this problem is attacked, one must find a soft film which can be acceptably perforated, since it must be perforated.

It is common experience that an edge of a sheet of paper can inflict a cut on whole skin. One can thus surmise that the edges of perforations in a plastic sheet, whether a hard, crystalline plastic such as polyethylene terephthalate, or a softer amorphous plastic such as poly(vinyl chloride), can be decidedly traumatic on a highly sensitive wound which is healing. In other words, there is insufficient "give" at the edge of a hole in a plastic sheet because prior art films lack the necessary elongation. This lack of "give" results in the periphery of a hole behaving like a knife-edge which produces a cutting action on tissue in contact with the periphery when the film is being removed. Even when there is only slight normal angular movement of the skin of the wounded person relative to the plane of the dressing, a lack of "give" and "softness" tends to produce some relative displacement between the film and the healing tissue, causing, at the very least, irritation, and often, considerable pain and trauma.

Films are perforated because an imperforate film, unless designed to have a water vapor transmission rate (WVTR) within a specified range, will generally provide neither adequate ventilation of the wound bed, nor passage of body fluids to the absorbent pad. Thus, it is essential for a film-faced wound dressing, to have essentially no restriction of fluid flow from the wound bed into the absorbent pad. To obtain this, the film is perforated with a multiplicity of closely spaced perforations, and irrespective of how good the release properties of a smooth, flexible plastic film such as has been used in the prior art for its good release properties, the sharp peripheries of holes in the film are highly objectionable because of the pain they inflict. By "sharp" I refer only to suitability for cutting and the ability to cut healing tissue, and not to peripheries which are so well-defined and free of jagged edges as to merit the designation "sharp".

As disclosed in the aforementioned '301 patent to Plantinga et al, there are limitations imposed on the perforations by the healing process. The size of the holes in the film must be quite small to prevent the neoespithelium or congealed exudate from adhering to the absorbent pad in the immediate vicinity of the holes. Yet, if too small, the holes are plugged with neoepithelium and decrease the effectiveness of the absorbent pad, the smaller the holes, the worse the plugging. Too many holes in prior art plastic film vitiate its physical integrity, and too few holes will interfere with the ventilation the film must provide. Even if one wanted a large open area with a very large number of holes per unit area, which may not be desirable, the holes in elastomeric films are not prone to being plugged, nor is the elastomeric film's integrity significantly impaired with a much larger ratio of open area to overall film area, compared with the ratio of open area to overall film area in plastic film.

The problem of patient comfort with sharp peripheral edges in punched film, and the inherently deleterious effect of the mechanical punching process on the tear resistance of the punched film have been well recognized. In U.S. Pat. No. 3,073,303, the film was thermally perforated so that portions of the film immediately adjacent and surrounding each of the perforations in the film are thicker than the remaining film. But the resulting film is too irregular and the raised peripheral edges contribute to severe discomfort in part attributable to the geometry of raised peripheries and in larger part attributable to the choice of polymers from which the film was made. Such polymers suggested for use included vinylidene chloride-vinyl chloride optionally plasticized, such as Saran 54L; polyethylene terephthalate such as Mylar; and crystalline polyethylene, because they are far more susceptible to being perforated thermally than elastomeric materials. My invention derives from discarding the use of raised peripheral edges, instead using a smooth, soft film which can be thermally bonded to an absorbent pad, and changing from a plastic film to an elastomeric one. By "smooth" I refer to the surface of the film which is essentially free of raised peripheral edges or crenelations. It was never heretofore realized that an elastomeric film can be so soft, and yet provide such good release with a concomitantly high comfort factor; nor that such a film, if satisfactorily perforated, would overcome the problems of the prior art films in film-faced wound dressings. Until the availability of perforated polyether polyurethane (PPU) film, this was not feasible. Such an elastomeric thin film has now been provided with uniformly spaced apart, uniform perforations which do not have jagged, crenelated, or built-up peripheries.

SUMMARY OF THE INVENTION

The perforations in a film-faced wound dressing in which the film is a soft self-supporting elastomeric film, have been discovered to have edges which, though clearly defined, lack the ability to cut the neoepithelium of a healing wound, with the result that the wound dressing affords an unexpectedly high degree of comfort during movement of the patient, and most particularly, when the dressing is changed. Such a film is obtained with a polyether polyurethane (PPU).

It is therefore a general object of this invention to provide a film-faced wound dressing with a film-face which has a degree of comfort and conformability not attached heretofore; which film-face has a softness and elastomeric quality which results in reduced shear associated with' the sharp cutting edges of perforations; which film-face has excellent release characteristics enhanced by less than 25% open area (due to perforations) which minimizes the open area into which the neopepithelium may grow, thus minimizes any cutting action of the film; all of which benefits associated with the film, result in faster wound healing, and, improved patient tolerance and attitude.

It has specifically been discovered that a thin, soft elastomeric film may be used to form a film-faced wound dressing, comprising, (a) an absorbent pad formed of a gas-permeable fabric of fibers held in place by interlocking and frictional engagement with each other, and, (b) a self-supporting soft elastomeric non-absorbent thin film, less than 2 mil thick, and preferably from about 0.5 mil to about 1 mil thick, of an essentially amorphous synthetic resinous, foraminous material thermally bonded to the lower surface of said pad, perforations in said film having open areas equal to a circle having a diameter in the range from about 0.01" (inch) to about 0.2" and being present in sufficient number and so distributed as to provide for each square inch of overall film surface, an open area of from about 0.05 in$^2$ to about 0.25 in$^2$, whereby the film may be placed in releasable contact with healing tissue.

It is a specific object of this invention to provide (i) a 'pad only dressing' consisting essentially of an absorbent pad of non-woven or woven fibers, the upper and lower surfaces of which pad are thermally bonded to upper and lower portions of thin, self-supporting soft elastomeric smooth non-absorbent perforated film portions lying coextensively with the pad;

(ii) a backed dressing, such as a finger bandage, consisting essentially of a laminar skin-conformable backing thermally bonded to the pad, with the backing having overhanging opposed ends the lower surfaces of which are coated with an adhesive for securing the dressing to the body of a patient; at least the lower surface of the pad, and preferably, both the upper and lower surfaces of the pad, are in turn, thermally bonded to self-supporting soft elastomeric smooth non-absorbent perforated portions (upper and lower) of thin film lying coextensively with the pad, so that the lower portion may be placed in contact with the wound;

(iii) a backed dressing consisting essentially of a laminar skin-conformable backing having one surface coated with a first adhesive for securing the pad to the backing which has overhanging opposed edges, the lower surfaces of which edges are coated with a second adhesive (which may be different in composition from the first, but is preferably the same) in a peripheral zone extending a predetermined width within the periphery of the backing, so that the second adhesive effectively secures the dressing to the body of the patient; and, (iv) any one of the foregoing dressings in which the absorbent pad contains a layer of flexible hydrophilic polymeric material in transversely spaced apart relationship with the thin film in contact with the wound, the function of which hydrophilic layer is to absorb exudate.

It is yet another specific object of this invention to provide a film-faced wound dressing in which the film is a polyurethane polymer which may be annealed for superior dimensional stability, and embossed with a pattern for greater product recognition because the embossing of the film results in a distinctive trade dress, and at the same time further reduces such proclivity of the film to stick to the wound, as the film may have.

BRIEF DESCRIPTION OF THE DRAWINGS

The foregoing and other objects and advantages of our invention will appear more fully from the following description, made in connection with the accompanying drawings of preferred embodiments of the invention, wherein like reference characters refer to the same or similar parts throughout the views and in which.

DETAILED DESCRIPTION OF A PREFERRED EMBODIMENT

Figure 1:
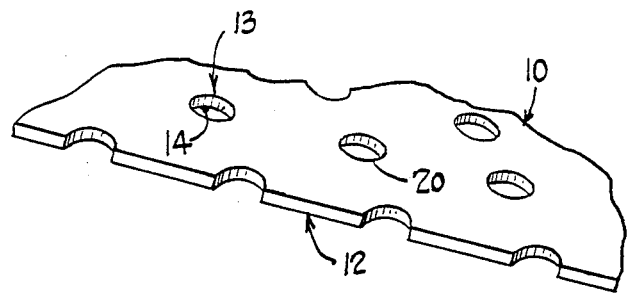
FIG. 1 is a perspective view, partially in cross section, showing the clearly defined peripheral edges of a perforate soft elastomeric film used in the film-faced wound dressing shown in FIG. 2.

Referring to the drawings, FIG. 1 is a perspective view schematically illustrating an elastomeric flexible self-supporting film, less than about 2 mil thick, and preferably in the range from about 0.5 mil to about 1 mil, indicated generally by reference numeral 10, to be used on the wound-contacting face of the dressing having upper and lower surfaces 11 and 12 respectively. This film is made by a conventional process as a continuous strip, in an arbitrary width, typically about 4 ft, which is a convenient width for economically producing a foraminous film with a multiplicity of perforations 20 having upper edges 13 in the upper surface 11, and lower edges 14 in the lower surface 12.

The essential characteristic of the elastomeric film is that it is thermally bondable to the absorbent fabric of the pad without the film being thermally degraded. The film is made from an elastomer of a synthetic rubbery material, preferably an amorphous (when unstretched) synthetic polymer of relatively high molecular weight (mol wt), preferably in the range from about 10,000 to about 1,000,000. Such a polymer returns rapidly to approximately initial dimensions and shape after substantial deformation by a weak stress and release of the stress. More specifically, we refer to a polymer which retracts within 1 minute to less than 1.5 times its original length after being stretched at room temperature (20° C.) to twice its length and held for 1 min before release. Elastomers particularly useful in is invention are-elastic at room temperature, that is, they are above their glass transition temperature (T$_g$). In contrast, prior art films have substantial crystallinity, are not elastomeric, and are used below their T$_g$ to preserve their dimensional stability.

The specific elastomer used will depend upon the material chosen for the fibers of the absorbent pad to which the film is to be thermally bonded at a temperature below that which is deleterious to the stability of the film. Most commonly used are fibers of cotton, polyesters, nylon and rayon. The problem is to find an elastomer film no more than 2 mils thick, which after being perforated, will be thermally bondable to the fibers of the pad without using an adhesive, not only without damaging the film, but also without vitiating the dimensional stability of the perforations. Still further, an adequate thermal bond requires that there be substantial mechanical compatibility between the elastomer and the fibers at the bonding temperature Suitable elastomers include ethylene-co-vinyl acetate; ethylene-co-methyl acrylate; butadiene-coacrylonitrile; isobutylene-co-isoprene; terpolymer of ethylene, propylene diene sidechain; ethyl acrylate-co-butadiene; brand urethanes formed by the reaction of (a) diisocyanates and polyalkylene polyether glycols, diisocyanates and polyalkylene polyester glycols; hycar brand butadiene-acrylonitrile modified with carboxyl groups; hydrin brand of epi-chlorodydrin with ethylene oxide; styrene-butadiene-styrene block copolymers available under the Kraton brand; hytrel brand copolyester, and the like, which are essentially liquid-impervious, do not absorb moisture, and can be formed into thin smooth-surfaced sheets in the range from about 0.5 mil to about 1 mil thick which will, after being perforated, substantially maintain the dimensional stability of the perforations after thermal bonding.

In the best mode of the invention, a soft thermoplastic elastomer having less than 10% crystallinity, said to possess "soft hand", is preferred. "Soft hand" refers to the characteristic feel of softness experienced when a sheet of soft film is crushed in one's hand. For such a soft film to be usable in film-faced wound dressings, the wound should have no adverse reaction to the film. Most preferred materials are the polyurethanes formed by a reaction of long chain polyols having a molecular weight of from 400 to about 10,000, preferably 800 to 6000, with diisocyanates and chain-extending agents (preferably short chain polyols), having molecular weights of up to 400, and the NCO/OH ratio is generally in the region of from 0.95:1 to 1.10:1.

Such long chain polyols include virtually all known polyesters, polylactones, polyethers, polythioethers, polyester amides, polycarbonates, polyacetals, and vinyl polymers which contain two Zerewitinoff active groups (mainly hydroxyl groups), with the optional addition of minor quantities of compounds of this type containing three Zerewitinoff active groups. Examples of such polyols include: polybutadiene diols, polyhydroxyl compounds already containing urethane or urea groups, modified and unmodified natural polyols and compounds containing other Zerewitinoff active groups, such as amino, carboxyl or thio groups. These compounds are known in the art and have been described in U.S. Pat. Nos. 3,963,679; 3,984,607; 4,035,213; inter alia.

Preferred linear polyols are derived from hydroxyl-containing polyesters of glycols or adipic acid, phthalic and/or terephthalic acid and the hydrogenation products therof, hydroxyl polycaprolactones, polyethylene oxide, polypropylene oxide, polytetrahydrofuran; and, mixed polyethers of ethylene oxide and propylene oxide.

Suitable diisocyanates for use according to the present invention include aliphatic, cycloaliphatic, aromatic, araliphatic and heterocyclic diisocyanates which are known in the art. The following are preferred for the purposes of this invention: hexamethylene diisocyanate, optionally with methyl substituents, isophorone diisocyanate and 4,4'-diphenylmethane diisocyanate (MDI).

Most preferred are the reaction product of polytetramethylene ether glycol and MDI, usually chain extended with an alkane diol having a number average mol wt in the range from about 10,000 to about 70,000. The excellent conformability of the film is attributable to its 50% stretch modulus which approximates that of human skin.

A quantitative characterization of a "soft" elastomer is one which has a Durometer A hardness less than about 40, and more preferably in the range from about 10-30. The hardness of a typical plastic film in a prior art film-faced dressing is measured in Durometer D or Rockwell M or R Series values which indicate much greater hardness than values on the Durometer A scale. (see *Fundamentals of Plastics and Elastomers* Table 7, pg 1-28 et seq.) In use for a film-faced wound dressing, a soft thin film is one which can be moved relative to the neoepithelium, with a minimum of tearing or cutting action due to perforations 20 through which some of the neoepithelium may protrude. Though difficult to quantify, the difference between a soft elastomer and one which is not, is easily and immediately apparent when a film-faced dressing with one or the other is removed from a healing wound.

Figure 2:
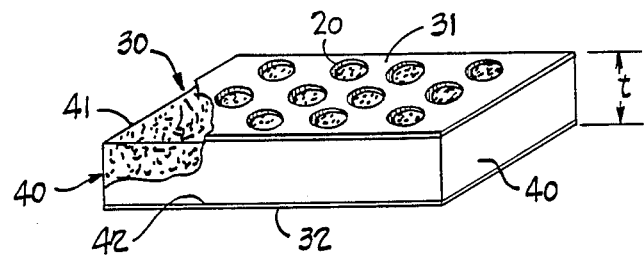
FIG. 2 is a perspective view, with a portion broken away, of the film-faced wound dressing in which the perforate soft film is thermally bonded to both the upper and lower surfaces of the absorbent pad.

Referring now to FIG. 2, there is shown a 'pad only' dressing, on an enlarged scale, indicated generally by reference numeral 30. The pad comprises a fabric 40, having upper and lower surfaces 41 and 42 respectively, and any desired arbitrary thickness 't', formed from woven or non-woven fibers held in place by interlocking and frictional engagement with each other. For a finger bandage the thickness t may be in the range from about 0.03" to about 0.125"; for other bandages for use on wounds on the abdomen and the like, t may range from about 0.125" to about 2" or even more, though there is generally no significant benefit to be gained from thicknesses greater than about 2".

Preferably the fabric is of plural layers of surgical cellulose crepe tissue, thermally bonded to perforate upper and lower film portions 31 and 32 respectively having perforations 20 (not visible for the lower portion 32). The pad may also be formed from one or more layers of woven fabric, such as woven cotton, the layers held in frictional engagement, one with the other.

Bonding of fabric to thin film, also referred to as "point-bonding", is effected by placing the pad in contact with the perforated film portions at a temperature sufficiently high to melt the surface of the film but not high enough to distort the peripheral edges of the perforations sufficiently to be visually noticeable. When this is done for a sufficient period of time to effect thermal bonding of the film to the pad, the bond obtained is such that the film cannot be separated from the pad without tearing the film or destroying the integrity of the pad. Such a strong bond is not adversely affected by continued contact with exudate, as is a non-thermal bond such as is obtained when the film is adhesively secured to the pad. And the strong thermal bond is characteristic of a superior film-faced wound dressing.

It is preferred, for expedience, that both the upper and lower surfaces of the pad be so bonded, though it will be apparent that the dressing will be effective with only a single film-faced surface in contact with the wound.

The ability of the elastomer to be thermally bonded to the absorbent pad obviates the necessity of coating the reverse face (the face of the perforated film away from the one in contact with the wound) of the film with an adhesive which is then contacted with the fibers of the pad.

Though, in the prior art, the thin film was formed of a crystalline polymer, not an elastomer, the step of coating the film with adhesive was a necessity if distortion of the perforations, either in the vertical or horizontal planes in the film, was to be avoided. Therefore thermal bonding was effected only in those instances where distortion of the perforations was not a consideration. Nor is it necessary to coat the film-face of my dressing with adhesive to keep it on the wound side if it can conveniently be bandaged to the body of the patient.

Figure 3:
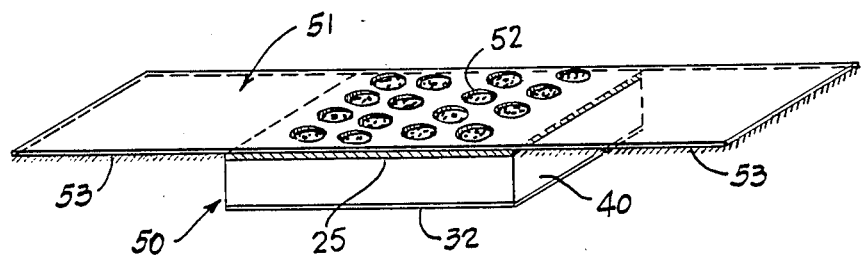
FIG. 3 is a perspective view of a finger bandage in which a perforate elongate backing is secured to a wound dressing (such as is shown in FIG. 2), in the absorbent pad of which is included a layer of flexible hydrophilic material to increase the absorption of exudate.

It may nevertheless be desirable to produce a "backed" dressing with the film-faced dressing of this invention, such as a finger bandage, indicated generally by reference numeral 50, diagrammatically illustrated in FIG. 3. Such a backed dressing consists essentially of a strip of backing with overhanging opposed ends, preferably of perforated film 51 with holes 52 preferably distributed substantially uniformly throughout at least that portion of the strip directly above absorbent pad 40, so that adjacent openings are substantially uniformly spaced from each other.

The pad 40 is faced on its lower surface with thin film 32 which is to be placed in contact with the wound. The upper surface of the pad (as shown) consists of fibers which are directly thermally bonded to the backing strip 51. The strip is preferably derived from an occlusive material which may be a non-porous film, and open-cell or closed-cell foam, a woven or non-woven fabric, or any combination of the preceding in the form of a laminate. Typically, the upper surface of fabric 40 will be thermally bonded to a thin perforated film which in turn will be directly bonded to the strip 51.

If desired, for additional absorptivity, the upper face of the pad may be coated with a layer 25 of non-toxic flexible hydrophilic material, preferably a crosslinked acrylic acid polymer in which a major proportion of the carboxylic acid groups are neutralized, as described in Canadian Pat. No. 1,160,984 issued January 24, 1984, the disclosure of which is incorporated by reference thereto as if fully set forth herein. As an alternative, the hydrophilic layer may be disposed intermediate the upper and lower faces of the pad. Though it will be evident that the function of absorbing exudate will be adequately met if the layer is transversely disposed relative to the upper and lower surfaces, the layer is preferably generally parallel, being formed by simply dipping a surface of fabric in the solution of monomer(s) which is then polymerized in situ. The thickness of the hydrophilic layer is not narrowly critical being determined by the size of the wound dressing in which it is used and the amount of exudate the dressing is expected to absorb. For small wound dressings the thickness may be as little as 5 mils, while for large dressings expected to absorb a large amount of exudate, the thickness may be in the range as high as from about 0.125" to about 0.25" (inch). When the layer 25 is formed as the upper surface of the pad 40, it may be either thermally bonded, or adhesively secured to the strip 51.

The strip film 51 may be formed from a skin-conformable material different in composition from, or the same as, that from which the thin film 32 is formed, and the strip is coated with an adhesive 53 near each of the strip's ends so as to allow the strip to be secured after it is wrapped around a finger. The first adhesive to secure the pad to the strip, and the second adhesive to secure the strip to the finger, may be different in composition, but is preferably the same. The thickness of the strip film is not critical, typically being in the same range as that of the thin film facing.

Though the finger bandage is illustrated with only a single thin film facing, it may also be made with both upper and lower thin film facings. This results, for example, an elongated absorbent pad (shown as a rectangular parallelepiped) in the thin film by placing the pad's lower surface on a portion of thin film at least as long as the pad. The longitudinal sides of the film are then raised over the corresponding edges of the pad and secured over its (the pad's) upper surface. The elongated pad is thus enveloped in a rectangular sleeve of thin perforate film. The pad, so enveloped may then be placed on a longer strip of backing the longitudinal edges of which may be folded over the sides of the enveloped pad and heat-sealed to the thin film on the lower face, near its edges so as not to cover a significant portion of the perforated thin film, in a method of making a finger bandage (which method is) analogous to one conventionally used.

Larger such backed dressings may be constructed with a relatively large dressing having a generally rectangular parallelepiped, circular, elliptical or any other suitable shape, and the dressing may be backed with one or more strips adhesively secured to it.

Figure 4:
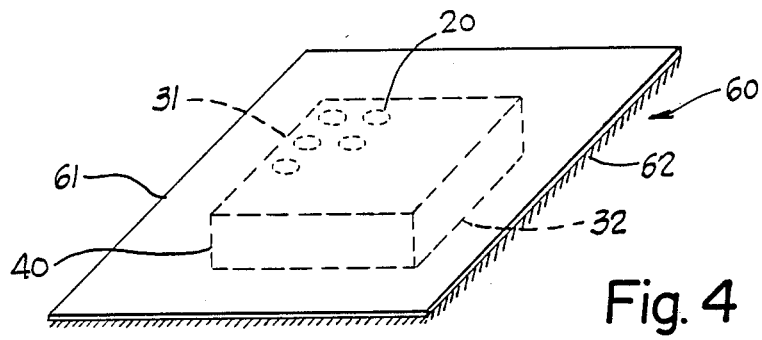
FIG. 4 is a perspective view of a backed dressing in which an imperforate backing is secured to a wound dressing (such as is shown in FIG. 2) to provide an overhanging border of backing to which border an adhesive coating is applied so that the backed dressing may e directly adhesively secured over the wound.

Referring to FIG. 4, there is schematically illustrated a typical relatively large backed dressing, indicated generally by reference numeral 60, consisting essentially of an absorbent pad 40, about 10 cm × 10 cm, the upper and lower surfaces of which are thermally bonded to upper and lower perforate film faces 31 and 32 respectively, coextensively with the pad's surfaces. The upper surface of film face 31 is adhesively secured with adhesive 62 to a backing 61 which overhangs the edges of the pad sufficiently to permit the boundary of the backing 61 to be adhesively secured to the body on opposed sides of the wound. The backing 61 may be perforate or imperforate, and either elastomeric or not, provided it has sufficient breathability and moisture vapor transmission to permit expeditious healing of the wound. Both requirements are typically met with a backing having a MVTR of at least 200 g, and more preferably from about 300 to about 1200 g of water per square meter per 24 hr at 50% relative humidity at 36° C. when measured in accordance with ASTM Proceduire E96–80.

Preferred adhesives are those conventionally used, such as those described in U.S. Pat. No. Re. 24,906 to Ulrich, particularly a copolymer of 96% iso-octyl acrylate and 4% acrylamide units, and a copolymer of 94% iso-octyl acrylate units and 6% acrylic acid units. Other useful adhesives are those described in U.S. Pat. Nos. 3,389,827 and 4,112,213, the disclosures of which are incorporated by reference thereto as if fully set forth herein. Adhesives may include medicaments to accelerate healing of the wound, salves, and the like.

Figure 5:
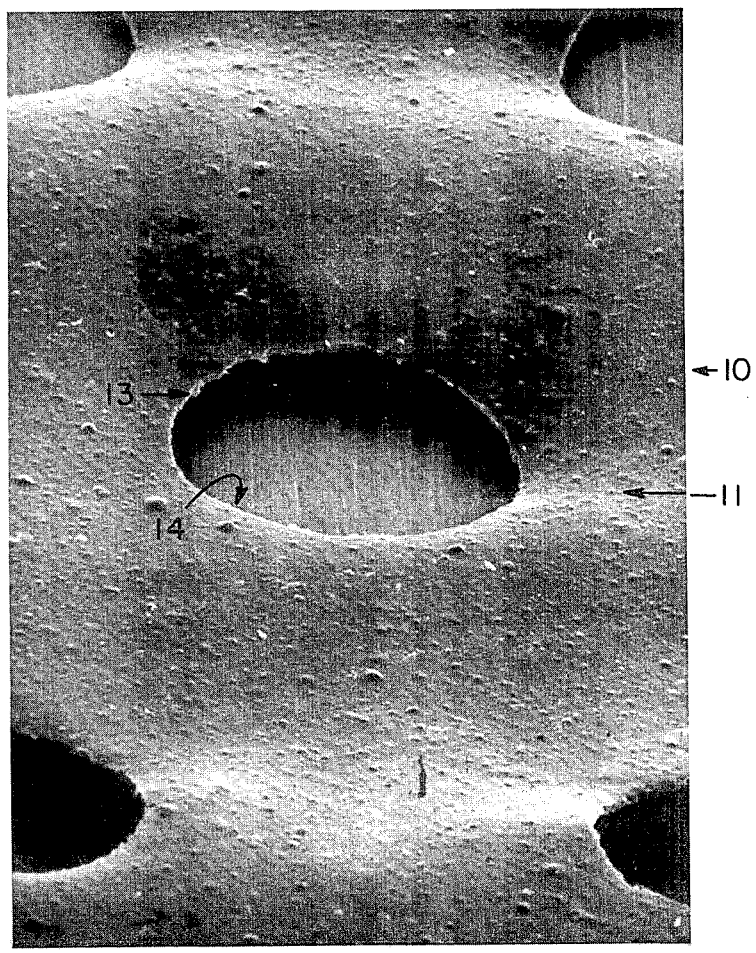
FIG. 5 is a photomicrograph of a portion of the film, in a perspective view, showing details of the perforations.

Referring to FIG. 5 there is shown a photomicrograph which is approximately a side elevational view corresponding roughly to that schematically illustrated in FIG. 1, showing a detail of a perforation, in which the upper edge 13 of the perforation's peripheral wall (thickness in the range from 0.5 mil to 1 mil) is essentially in the same plane as that of the upper surface 11 of the film 10; and the lower edge 14 of the peripheral wall is essentially in the same plane as that of the lower surface 12 of the film. It is evident that the vertical distortion (distortion in the vertical direction) of the wall of the periphery is less than 50% of the thickness of the film. The precise amount of the distortion will depend upon the type of punching means, whether a continuous rotary punching means or an intermittent planar one, the sharpness of the individual punching elements, the thickness of the film, the temperature at which the film is punched, and other factors, but will not exceed 50%.

Though the lateral distortion of the perforation is not narrowly critical, it is to be small so as not to be visually so easily noticeable as to be displeasing in the finished dressing. The particular choice of elastomer will be the major factor in the distortion obtained, and with the afore specified polyurethanes is limited to about 30% of the specified average major axis of a perforation, which, when the perforations are circular, is the diameter. This lateral distortion may be further minimized by annealing the film, prior to punching it, to relieve stresses in the film produced by the method of its formation. The annealing temperature of each elastomer will vary, but is generally lower than, and within about 20° C. of its melting point. The most preferred polyurethane films have an annealing temperature in the range from about 85° C. to about 115° C.

I claim:

1. A film-faced wound dressing, comprising,
   (a) a pad of absorbent gas-permeable fabric formed of fibers held in place by interlocking and frictional engagement with each other, to which fabric is directly attached
   (b) an elastomeric, soft, substantially non-absorbent, foraminous thin polyurethane film, less than 2 mil thick, free of adhesive on its lower surface which is to contact the wound, thermally pout bonded to the lower surface of said pad, each perforation in said film having open areas equal to a circle having a diameter of 0.01 to 0.05 of an inch and free of sharp edges, said perforations being present in sufficient number, and so distributed, as to provide for each square inch of overall film surface, an open area in the range from more than about 0.05 in$^2$ but less than about 0.25 in$^2$, said perforations characterized by the upper edge of perforation's wall being essentially in the same plane as that of the upper surface of the film;
   whereby when said film-faced wound dressing is disposed on the wound with said film placed in contact with healing tissue, said film is releasable from the wound without the peripheral edges of the perforations cutting the healing tissue.

2. The wound dressing of claim 1 wherein said fibers are formed from a material selected from the group consisting of cotton, polyester, nylon and rayon.

3. The wound dressing of claim 1 wherein the upper and lower surfaces of said fabric are each thermally bonded to said foraminous thin polyurethane film portions.

4. The wound dressing of claim 1 wherein said fabric of fibers includes a layer of flexible hydrophilic polymeric material in transversely spaced apart relationship with said polyurethane thin film to be placed in contact with the wound, so that the layer of polymeric material absorbs exudate.

5. The wound dressing of claim 2 wherein said fabric is a non-woven fabric.

6. The wound dressing of claim 2 wherein said fabric consists essentially of plural layers of woven fabric held in frictional engagement one with the other.

7. The wound dressing of claim 2, including,
   (c) a laminar skin-conformable backing thermally bonded to said pad, said backing having overhanging opposed ends the lower surfaces of which are coated with an adhesive for securing said dressing to the body of a patient.

8. The wound dressing of claim 2, including,
   (c) a laminar skin-conformable backing having one surface coated with an adhesive for adhesively securing said pad to said backing, said backing having overhanging opposed ends the lower surfaces of which are coated with an adhesive in a peripheral zone extending a predetermined width within the periphery of said backing so that the adhesive in said zone effectively secures said dressing to the body of a patient.

9. The wound dressing of claim 2 wherein said polyurethane film is derived from linear polyols in turn derived from hydroxyl-containing polyesters of glycols or adipic acid, phthalic and/or terephthalic acid and the hydrogenation products thereof, hydroxyl polycaprolactones or polytetrahydrofuran and a diisocyanate; said polyurethane film is annealed to relieve residual stresses, so that the length along a major axis of each said perforations is the average specified length of said major axis, after thermal point bonding of the film to the absorbent pad.

10. The wound dressing of claim 9 wherein the upper peripheral edges of said perforations are essentially in the same plane as that of the upper surface of said polyurethane film, and, the lower peripheral edge of said perforation is essentially in the same plane as that of the lower surface of said film.

11. The wound dressing of claim 10 wherein the periphery of each said perforation is circle and said major axis is its diameter.

12. The wound dressing of claim 10 wherein the periphery of each said perforation is an ellipse.

13. The wound dressing of claim 10 wherein said polyurethane film is embossed with an identifying pattern.

14. The wound dressing of claim 2 wherein said polyurethane film is derived from linear polyols in turn derived from hydroxyl-containing polyesters of glycols or adipic acid, phthalic and/or terephthalic acid and the hydrogenation products therof, hydroxyl polycaprolactones, or polytetrahydrofuran; a short chain polyol chain extender; and a diisocyanate; said polyurethane film is annealed to relieve residual stresses, so that the length along a major axis of each said perforations is ±20% the average specified length of said major axis, after thermal point-bonding of the film to the absorbent pad.

* * * * *